United States Patent [19]

Lord

[11] Patent Number: 5,318,503

[45] Date of Patent: Jun. 7, 1994

[54] METHOD AND APPARATUS FOR AUDITORY AND OLFACTORY RELAXATION

[76] Inventor: Robert F. Lord, 21931 Tobarra, Mission Viejo, Calif. 92692

[21] Appl. No.: 813,647

[22] Filed: Dec. 27, 1991

[51] Int. Cl.⁵ .......................................... A61M 21/00
[52] U.S. Cl. .......................................................... 600/27
[58] Field of Search ...................................... 600/26–28

[56] References Cited

U.S. PATENT DOCUMENTS

| | | | |
|---|---|---|---|
| 3,826,250 | 7/1974 | Adams | 600/28 |
| 4,640,266 | 2/1987 | Levy | 600/27 |
| 4,893,615 | 1/1990 | Khabirova | 600/28 |

Primary Examiner—Lee S. Cohen
Assistant Examiner—John P. Lacyk
Attorney, Agent, or Firm—John E. Vanderburgh

[57] ABSTRACT

The method of the present invention consists of generating a repetitious sound which is intended to be repeated by the user to focus mental concentration on an audible focal point and concurrently with the generation of the repeated sound, releasing a fragrance which over repeated use will become associated in the mind of the user with a relaxed state which is induced by the constant repetition of the sound. The apparatus of the present invention includes means for generating a sound at timed intervals to initiate the relaxation state and means for generating a fragrance which becomes associated in the mind of the user with the relaxed state induced by the sound. Means are also provided for amplifying the sound so that it is audible to the user of the device. The sound generating means, the fragrance diffusion means and the audible means are combined in a headset which further includes at least one ear piece which is fitted over the ear of the user. The fragrance diffusing means is incorporated into the headset for diffusion of the fragrance while the sound is being transmitted to the user. The fragrance is produced by essential oils derived from various plants which have a pleasing and relaxing fragrance or a blend of such oils.

3 Claims, 2 Drawing Sheets

METHOD AND APPARATUS FOR AUDITORY AND OLFACTORY RELAXATION

FIELD OF THE INVENTION

This invention relates to the inducement of a state of relaxation and stress relief more particularly to relaxation and stress relief by auditory and olfactory stimulation.

BACKGROUND OF THE INVENTION

Much has been written in recent years concerning the adverse effect that stress, induced by modern-day living, particularly in urban areas, has upon the health and welfare of a human being. It has now been established that stress caused by an upheaval in a person's life such as a divorce or the like, loss of a job, change of location and similar events, often will produce stress which precedes serious illness such as cancer, stroke or heart disease.

Numerous books have been written on ways to relieve stress and anxiety. In addition, exercise systems, biofeed back systems and the like have been developed to aid a person to obtain both physical and mental relaxation. Normally, such systems are employed in conjunction with physical devices which are designed to stimulate the senses, particularly the sense of sight and sound, of the individual seeking relaxation. Such devices are generally intended to provide an environment for the individual which shuts out outside interferences.

Some devices go as far as to provide an enclosure for the individual and to bombard the individual's senses while in the enclosure for the purpose of inducing relaxation, both physical and mental (U.S. Pat. No. 4,640,266). Other devices have been employed which are less elaborate but which generally involve a device which includes a headset for transmitting sound and means for providing a visual display in conjunction with the sound.

Of the prior art devices only one, an enclosure described in U.S. Pat. No. 4,640,266 discloses any means for stimulating the olfactory senses of the user. However, with such a device, the user must be within the enclosure during which he is also subjected to visual as well as auditory stimulation.

The prior art devices which aid in inducing a state of relaxation, can generally be classified as "passive", that is to say they require no participation by the user. Consequently, the prior art devices often will induce a state of hypnosis or sleep, which goes beyond stress relief and relaxation. In addition, all the prior art devices require a visual display and thus require means for making such a display such as a video screen or the like which can be bulky and inconvenient to transport.

SUMMARY OF THE INVENTION

It is an object of the present invention to provide a device for inducing a relaxed state and for the relief of stress with which the user can be actively and mentally involved in the process.

Another object of the invention is to provide a method for stress-relief and relaxation which involves the stimulation of the sense of hearing and the sense of smell.

Yet another object of the invention is to provide a device for relaxation and stress-relief which is compact and readily transported so that it may be used even while traveling.

Another object of the invention is to provide a method for stress-relief and relaxation which takes advantage of the relaxation inducement of certain fragrances and which takes advantage of the close relationship between memory and the sense of smell so that the particular fragrance will be associated in the mind of the user with relaxation.

The foregoing objects are achieved by the method of the present invention which comprises generating a repetitious sound which is intended to be repeated by the user to focus mental concentration on an audible focal point and concurrently with the generation of the repeated sound, releasing a fragrance which over repeated use will become associated in the mind of the user with a relaxed state which is induced by the constant repetition of the sound.

The apparatus of the present invention comprises means for generating a sound at timed intervals to initiate the relaxation state and means for generating a fragrance which becomes associated in the mind of the user with the relaxed state induced by the sound. Means are also provided for amplifying the sound so that it is audible to the user of the device. The sound generating means, the fragrance diffusion means and the audible means are combined in a headset which further includes at least one ear piece which is fitted over the ear of the user. The fragrance diffusing means is incorporated into the headset for diffusion of the fragrance while the sound is being transmitted to the user. The fragrance is produced by essential oils derived from various plants which have a pleasing and relaxing fragrance or a blend of such oils. Such oils are sufficiently volatile to readily emit a fragrance when atomized in a stream of air or when a stream of air is passed over a container of the essential oil or an adsorbent material impregnated with the essential oil. As mentioned, the fragrance is generated in conjunction with the repetitious sound so that the relaxed state which is induced by the sound and by the repeating of the sound by the user becomes associated in the user's mind with the fragrance and thus reinforces the obtainment of the relaxed state. Preferably, both the generation of the sound and of the fragrance are electronically controlled with circuitry carried on the headset. The device of the present invention is compact and readily transported in a purse or briefcase or the like and is readily available for use even as one is travelling.

These and other objects and features of the present invention will become apparent from the following detailed description taken in conjunction with the figures.

DESCRIPTION OF THE INVENTION

Figure 1:
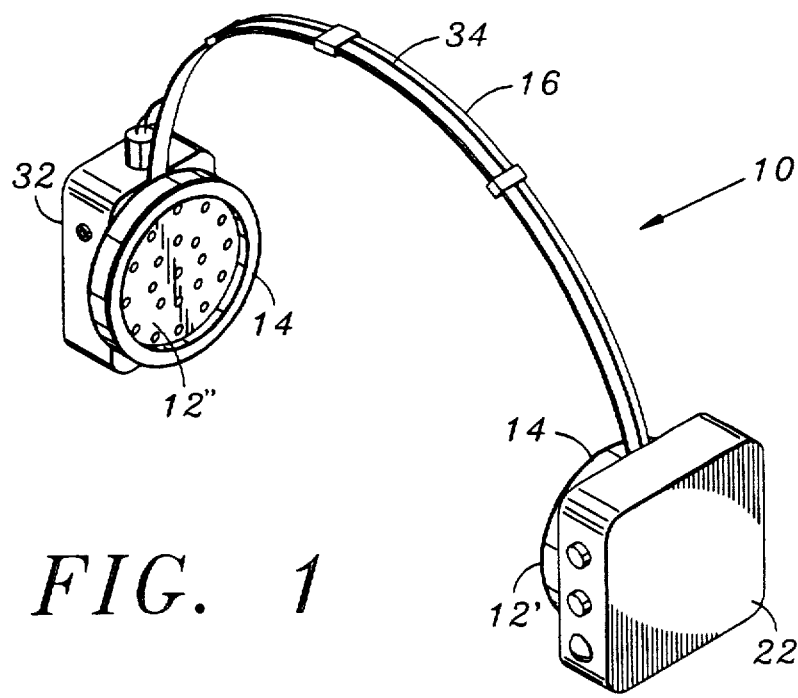
FIG. 1 is a perspective view of a headset incorporating the stress and relaxation inducer of the present invention.

Aromatherapy is a term used to describe the use of essential oils and more particularly the fragrance or aroma from the essential oil to promote the nature treatment of various bodily and psychic disfunction. It is well known that fragrances can induce a state of mine such as a pleasant sensation, as is well evidenced by the art of perfumery. The expansion of modern aroma therapy began in Europe in 1964 with the publication of the book "aromatherapie", which has been translated in the English under the name "The Art of Aromatherapy Healing", Arts Press, Rochester, Vermont, 1982.

Essential oils are highly concentrated vegetal extracts from certain plants and they are characterized by being volatile oily substances normally found as tiny droplets between plant cells. Essential oils are produced by a number of different processes including solvent extraction, pressing and distillation, for example.

Although the term aromatherapy would imply that the use of the essential oils is based solely on their fragrance, in fact practitioners of aromatherapy use a variety of different methods of application including use in ointments and creams, wet packs and the like. For the purposes of this invention, however, diffusion is the method of application of the essential oil. Diffusion is used to mean any method of inducing the fragrance of the essential oil into the atmosphere such as by nebulization and/or where the droplets of essential oil are dispersed into the atmosphere or by simply exposing the essential oil to a stream of air to cause volatiles from the essential oil to be carried in the stream of air into the atmosphere.

The essential oils are rather low molecular weight, oily volatile substances derived from plants. These substances are terpene based or phenylpropane derivatives which are substituted with various functional groups, such as ketone, aldehyde, ester, alcohol and the like groups which give the various essential oils their characteristic properties. Generally speaking the essential oils have a backbone of less than 20 carbon atoms and more commonly less than 15 carbon atoms. The essential oils may be produced from practically all parts of a plant. For example, by distillation of blossoms, such as neroli (orange blossom) and rose, jasmine and narcissi. Essential oils are also derived from plant seeds such as the seeds of citrus fruits, anise, fennel and coriander. Trees and bushes also create oil in the wood, such as for example, sandal wood, cedar wood or produce odorless resins and gums such as myrrh, frankincense and the like. Other essential oils are derived from the leaves of plants such as for example from the leaves of the eucalyptus and peppermint.

In accordance with the theories of aromatherapy, certain essential oils or blends of essential oils, are known to effect different parts of the body. Thus, certain essential oils are known to be effective in the relief of stress and in the inducement of relaxation. Table A sets forth a group of these essential oils known to have this property and the plant source for these oils.

TABLE A

| Essential Oil (common name) | Source (Plant) |
| --- | --- |
| Benzoin Resinoid | Styrax Benzoin |
| Bergamot | Citrus bergamia |
| Chamomile | Anthemis Nobilis |
| Cistus | Cistus landaniferus |
| Cedarwood | Cedrus Atlantica |
| Fur | Abies Balsema |
| Frankincense | Boswellia Carteri |
| Jasmine | Jasminum Officinalis |
| Lavender | Lavandula Officinalis |
| Lemon | Citrus Limonum |
| Marjoram | Origamum Marjorama |
| Melissa | Melissa Officinalis |
| Myrrh | Commithora Myrrha |
| Neroli | Orange Blossom |
| Patchouli | Pogostemon Patchouli |
| Peppermint | Menth Piperita |
| Petitgrain | Bitter Orange Leaves |
| Pine | Pinus Sylvesters |
| Rose | Rosa Centifolia and Damascena |
| Rosemary | Rosmarinus Officinalis |
| Rosewood | Aniba Roseaodora |
| Sage | Salvia Officinalis |
| Sandalwood | Santalum Album |
| Spruce | Picea Mariana |
| Tangerine | Tangerine Peel |
| Thyme | Thymus Vulgaris or Thymus Hiemalis |
| Ylang Ylang | Unona Odorantissimum |

It will be understood although the foregoing essential oils can be used alone, it is often preferable to prepare a blend of different essential oils to prepare a fragrance most pleasing to an individual. Thus it will be seen that the particular blend of essential oils is a matter of choice depending on the individual. It is important that the particular fragrance used be pleasing to the user so that an association between the fragrance and a sense of relaxation and release of stress be developed in the mind of the user.

While the fragrances of the aforementioned essential oils are known for their tendency to induce relaxation and relieve stress when sensed by an individual, the generation of a repetitious sound produces an audio stimulation in individuals which can also produce a sense of relaxation and in fact in certain cases can induce sleep. There are various types of soothing sounds that can be produced electronically to induce relaxation such as for example sounds simulating rain or ocean surf and even so-called "white noise" which is noise generated having a preselected frequency which is designed to coincide with brainwave patterns. Such sounds are known to have a relaxing effect when listened to for a period of time.

In accordance with the present invention there is provided a compact unit which is adapted to be worn by a user, in the manner of a headset, and which is capable of generating a repetitious sound designed to promote relaxation and stress relief. In addition, however, the unit of the present invention further coordinates the sound with the release of a fragrance from an essential oil or a blend of essential oils selected for their relaxation and stress relieving characteristics and which are pleasing to the user. Unlike the prior art devices, the user is encouraged to actively participate with the device of the present invention by repeating the sound generated by the device. In this fashion the user is encouraged to concentrate his thoughts on the sound, a technique which is utilized by those who engage in meditation. For the purposes of this description, the repetitious sound will be referred to as a "mantra".

Referring to FIG. 1, the device of the present invention, shown generally as 10, consists of earphones 12' and 12" which are provided with a padding material 14 to comfortably fit over the ears of the user. The earphones 12' and 12" are interconnected by a strap 16 which is contoured to fit over the top of the user's head and which is formed in two or more sections 16a and 16b which are slidably held by clamps 18 for adjustment of the length of the strap 16 to accommodate the size of the user's head. The outer surface 20 of the earphone 12' carries a case 22 for control and sound generation circuitry (FIG. 2) which is described in more detail below. A speed-control switch 24, a volume control 26 and a function control switch 28 are provided on one face of the case 22 and are electronically connected to the circuitry for control of the device 10. The outer surface 30 of the opposite earphone 12" carries a diffuser 32, for releasing the fragrance of an essential oil or blend of essential oils contained in the diffuser 32. Wires 34 are carried by the strap 16 for connecting the control circuitry in the case 22 to the diffuser 32 and the earphones 12' and 12".

Figure 2:
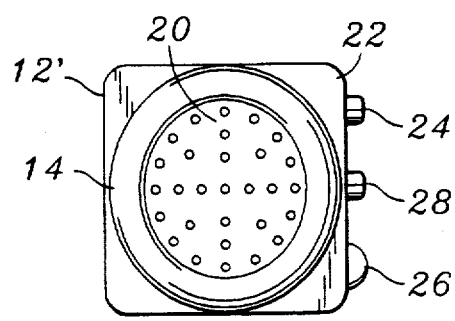
FIG. 2 is a side-elevation of one earpiece illustrating the earphone and case for the circuitry and controls for the device of FIG. 1.

The circuitry for controlling the operation of the device is schematically illustrated in FIG. 2. A control panel 36 is connected to a source of power 38 and at 40 to ground. The control panel 36 is connected to a central processing unit (CPU) 42, such as an 8084 CMOS chip, by leads 72 and 76 through a an analog-to-digital converter 74 and a gate 78. A clock 50 is connected to the CPU 42 by leads 48 and 52. The desired mantra or sounds are stored in digitized form in memory 54, provided by an "E" type prom, which is connected by leads 56 and 58 to the CPU 42. The clock 50 signals the CPU 42 to pull the sound from the memory 54 which is then transmitted through a lead 60 to a digital-to-analog converter 62 and amplifier 64 to the audio output 66, in this case the earphones 12' and 12". A lead 68 from the digital-to analog converter 62 to the clock 50 carries a signal indicating that a sound has been processed.

To enable the active participation by the user, the user repeats the sound which is input by an audio input 70, such as a microphone, to the control panel 36 through a lead 72 and is digitized by the analog-to-digital converter 74. The digital signal passes through the lead 76 and the gate 78 which determines whether the device 10 is in an active or a passive mode of operation. As illustrated, the gate 78 is positioned for the active function so that the input signal passes through a lead 80 and enabler gate 82 which is also connected to the clock 50 by lead 84 and to the CPU 42 by a lead 86. If desired, the gate 78 can be switched by a signal from the CPU 42 so that audio input goes directly to the CPU 42 by a lead 88 and to memory 54 for programming purposes. This is controlled by the function switch 28 through the control panel 36 and a lead 90.

In a preferred embodiment, the clock 50 also functions to transmit a timed signal to the CPU 42 for control of the diffuser 32 through the lead 48.

In operation, the user selects the function, active or passive, by the function control switch 28 which provides a signal through the lead 90, CPU 42 and a lead 92 to control the switch position of the gate 78. In the active mode, which requires the active participation of the user, i.e., the audible repeating of the mantra produced by the device, the gate 78 is connected to the CPU 42 through the lead 80, the enabler gate 82 and the lead 86. Upon activation of the device 10, the CPU 42 calls the first sound increment from memory 54 which is transmitted through the lead 60 to the digital-to analog converter 62 for conversion to a digital signal and the amplifier 64 to the audio output 66. At the same time a signal is generated by the digital-to analog converter 62 to the clock 50 to start the timing of the interval to the next sound generation cycle. The user repeats the sound through the audio input 70 and analog-to-digital converter 74 and the digitized signal is then transmitted through the lead 80 to the enabler 82 which signals the clock 50 that it has received the signal. If the signal is received within a preselected time period the clock 50 issues the signal to the CPU 42 and the sound generation process is repeated. If, however, the clock 50 is not signaled within the preselected time by the digital-to-analog converter 62, the enabler 82 opens the circuit between the gate 78, lead 80 and the enabler 82 interrupting the sound generation cycle and the CPU 42 is programmed to pull from memory 54 a prerecorded digitized message which is sent through the line 60, the digital-to analog converter 62, the amplifier 64 to audio output 66 to remind the user to repeat the sound. Receipt of the second message through the digital-to-analog converter 62 causes it to again issue the signal to the clock 50 that a sound has been processed and the enabler 82 is returned to its normal mode, the mantra producing signal is then repeated in the manner described.

If the user desires to change the mantra the function control switch 28 can be activated to send a signal through the lead 90 to the CPU 42 which switches the enabler gate 82 to break the circuit between the enabler gate 82 and the clock 50 through the lead 84. The mantra generating cycle continues regardless of signals, or lack thereof, from the digital-to-analog converter 62.

To program a new sound or mantra the function selector switch is positioned to signal the gate 78 through the lead 92 to complete the circuit from the audio input 70 directly to the CPU 42 through the analog-to-digital converter 74 and the gate 78. The new mantra is then directly input through the CPU 42 to the memory 54. The function switch 28 can then return to its original position which throws the switch in the gate 78 to restore the timing circuitry as previously described.

In the preferred embodiment, the CPU 42 is programmed so that the intervals between sound generation increase over a period of time to accommodate the user as he becomes more and more relaxed. In this connection the CPU 42 is programmed to increase the timing intervals over the period that the device is in use. Also, in the preferred embodiment, the CPU 42 is programmed to control the fragrance generator in response to preselected time signals from the clock 50. Thus, for example, the CPU 42 is programmed to signal the fragrance generator to emit fragrance each five to ten seconds during operation of the device. It will be understood, however, that the preferred sequence of fragrance emissions is a matter of choice and the aforementioned time interval is not critical. It will be further understood that the fragrance diffuser may be manually operated so that no signal from the CPU 42 to the fragrance diffuser is required. However, automatic operation of the fragrance diffuser is highly preferred.

Figure 4:
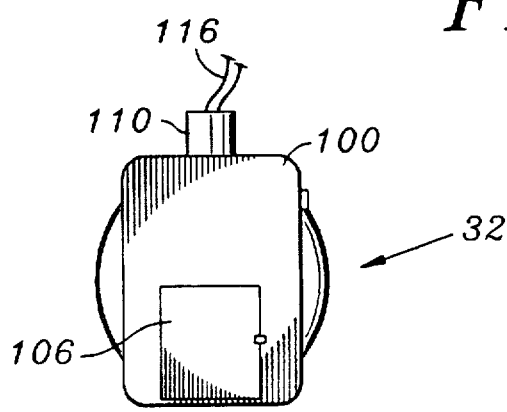
FIG. 4 is a side-elevation of the earpiece opposite the earpiece illustrated in FIG. 2 showing the container for the fragrance generator.
Figure 5:
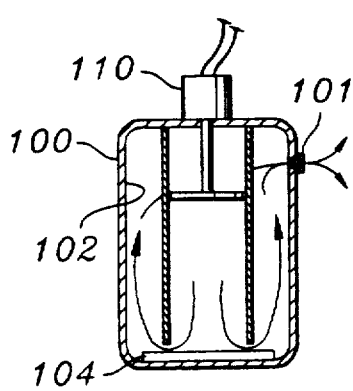
FIG. 5 is a sectional view of the container for the fragrance generator illustrated in FIG. 4.
Figure 3:
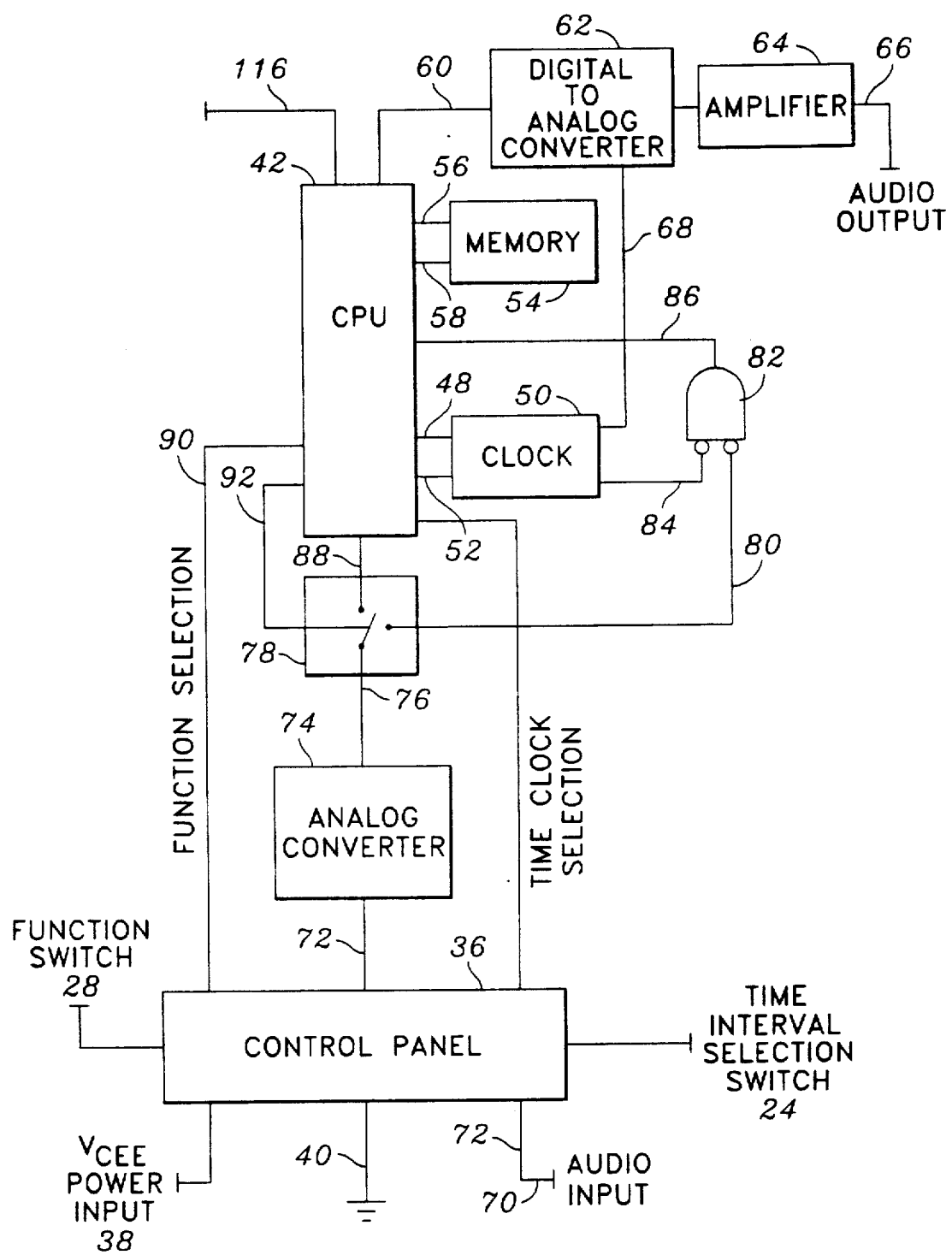
FIG. 3 is a schematic diagram of the sound inducement circuitry and controls therefore.

Referring now to FIG. 4 and 5, the fragrance diffuser 32, includes hollow housing 100 which defines a chamber 102 for containing the essential oil. An opening 101 communicates from the exterior of the housing 100 into the chamber 102. The chamber 102 can serve as a reservoir in which the essential oil is held as a liquid or, as illustrated, as a container for a saturated pad 104 of absorbent material which has been saturated with the essential oil or blend of essential oils. An access door 106 is provided in the housing 100 for access to the chamber 102 for the introduction of the essential oils. In the embodiment illustrated a cylinder 108 extends from the top of the housing 100 to a point just adjacent the bottom of the chamber 102. The cylinder 108 terminates so that its lower end is spaced above the level of the essential oil or the pad 104 containing the essential oil to allow for contact between air and the essential oil. An electrically controlled solenoid 110 is carried on the top wall of the housing 100 and is connected to a piston 112 within the interior of the cylinder 108. Upon receipt of a signal from the CPU 42 the solenoid 110 is activated to move the piston 112 downwardly in the cylinder 108 to create a positive pressure within the cylinder 108. The force of the piston 112 moves air past the essential oil reservoir picking up the fragrance from the essential oil where it is then carried in the air into the chamber 102 and thence to the outside of the diffuser 32 through the outlet 101. Upon completion of its downward stroke, the solenoid 110 draws the piston 112 back to its normal position which reduces the pressure within the chamber 102 and air is drawn in through the outlet 101 to equalize the pressure within the chamber 100. The solenoid 110 is electrically connected to the control circuitry for the receipt of signals therefrom by a lead 116.

It will be understood that the fragrance diffuser 32 may be manually operated and in such a case the electrically operated solenoid 110 is replaced with a manually operated plunger (not shown). In all other respects, however, the operation of the fragrance diffuser is the same as described.

From the foregoing description it will be seen that the device of the present invention combines the beneficial effects of relaxing and repeated sound and fragrances which are known to induce a state of relaxation in an individual. The device is programmed to respond to the users participation and to remind the user that he should participate in order to more effectively focus and concentrate his thoughts. By repeated, use the fragrance and the sounds will become associated in the mind of the user with a state of relaxation and lowered stress so that over a period of time the fragrance itself may be sufficient to induce the state of relaxation and lowered stress achieved with the use of the device. It will also be understood that after repeated use, the audio input feature of the device can be deactivated so that it is not necessary for the user to audibly repeat the mantra in order to have the device continue to operate.

As will be understood by those in the art, various arrangements other than those described in detail in the specification will occur to those persons skilled in the art, which arrangements lie within the spirit and scope of the invention. It is, therefore, to be understood that the invention is to be limited only by the claims appended hereto.

Having described the invention, I claim:

1. A compact transportable combination of auditory and olfactory stimulants for relaxation and stress relief, said combination consisting of:
   means for producing in times repetition a signal representative of a sound for focusing the attention of a user on an audible focal point;
   means for receiving said signal comprising a headset adapted to be worn by the user which includes a strap and at least one earpiece for receiving said signal;
   a container for an essential oil carried by said earpiece, said container including means for diffusing a fragrance of said essential oil periodically from said container;
   circuitry connecting said headset and said means for producing a signal whereby the repetitious signal and fragrance become associated in the mind of the user to reinforce the attainment of a relaxed, stress-free state.

2. The combination of claim 1 wherein said means for diffusing the fragrance of said essential oil comprises an atomizer for diffusing said essential oil into the atmosphere.

3. The combination of claim 1 wherein said means for diffusing the fragrance of said essential oil comprises an essential oil permeated absorbent material in said container and a hinged cover on said container which is opened to permit the fragrance of said essential oil to diffuse into the atmosphere from said container while said cover is open.

* * * * *